United States Patent

Gyory et al.

[11] Patent Number: 5,990,179
[45] Date of Patent: *Nov. 23, 1999

[54] COMPOSITION AND METHOD OF ENHANCING ELECTROTRANSPORT AGENT DELIVERY

[75] Inventors: J. Richard Gyory, San Jose; Patricia S. Campbell, Palo Alto, both of Calif.

[73] Assignee: ALZA Corporation, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/431,187

[22] Filed: Apr. 28, 1995

[51] Int. Cl.$^6$ .................................................. A61K 9/08
[52] U.S. Cl. ......................... 514/970; 514/329; 514/946; 514/947; 564/194; 604/20
[58] Field of Search .................... 424/449; 514/946, 514/329, 817, 818, 970; 604/20; 564/191, 194

[56] References Cited

U.S. PATENT DOCUMENTS

| | | | |
|---|---|---|---|
| 4,555,524 | 11/1985 | Grubert et al. | 514/570 |
| 4,558,690 | 12/1985 | Joyce | 128/1 R |
| 4,593,053 | 6/1986 | Jevne et al. | 523/111 |
| 4,605,670 | 8/1986 | Saito et al. | 514/619 |
| 4,637,930 | 1/1987 | Konno et al. | 424/28 |
| 4,685,911 | 8/1987 | Konno et al. | 604/897 |
| 4,722,726 | 2/1988 | Sanderson et al. | 604/20 |
| 4,722,941 | 2/1988 | Eckert et al. | 514/784 |
| 4,731,241 | 3/1988 | Yamada et al. | 514/227 |
| 4,752,285 | 6/1988 | Petelenz et al. | 604/20 |
| 4,820,263 | 4/1989 | Spevak et al. | 604/20 |
| 4,879,119 | 11/1989 | Konno et al. | 424/449 |
| 4,879,274 | 11/1989 | Kamiya et al. | 514/12 |
| 4,882,163 | 11/1989 | Guse et al. | 424/448 |
| 4,888,354 | 12/1989 | Chang et al. | 514/424 |
| 4,892,737 | 1/1990 | Bodor et al. | 424/449 |
| 4,927,408 | 5/1990 | Haak et al. | 604/20 |
| 4,940,456 | 7/1990 | Sibalis et al. | 604/20 |
| 4,950,229 | 8/1990 | Sage, Jr. | 604/120 |
| 4,952,560 | 8/1990 | Kigasawa et al. | 514/2 |
| 4,959,365 | 9/1990 | Francoeur et al. | 514/237.5 |
| 4,973,303 | 11/1990 | Johnson et al. | 604/20 |
| 5,001,139 | 3/1991 | Lawter et al. | 514/344 |
| 5,023,085 | 6/1991 | Francoeur et al. | 424/449 |
| 5,026,556 | 6/1991 | Drust et al. | 424/449 |
| 5,045,319 | 9/1991 | Chien et al. | 424/448 |
| 5,045,553 | 9/1991 | Ueda et al. | 514/344 |

(List continued on next page.)

FOREIGN PATENT DOCUMENTS

| | | | |
|---|---|---|---|
| 0278473 | 8/1988 | European Pat. Off. | A61K 37/02 |
| 0448300 | 9/1991 | European Pat. Off. | A61N 1/30 |
| 0552879 | 7/1993 | European Pat. Off. | A61K 47/10 |
| WO8900853 | 2/1989 | WIPO | A61K 31/60 |
| WO9008507 | 8/1990 | WIPO | A61B 10/00 |
| WO9116077 | 10/1991 | WIPO | A61K 47/12 |
| WO9301807 | 2/1993 | WIPO | A61K 9/70 |
| WO9506497 | 3/1995 | WIPO | A61N 1/30 |

OTHER PUBLICATIONS

Srinivasan et al., J. Pharm. Sci. 79(7):588–91 (1990).

Primary Examiner—Robert H. Harrison
Attorney, Agent, or Firm—D. Byron Miller; Steven F. Stone

[57] ABSTRACT

A composition suitable for transdermal electrotransport delivery of an agent through a body surface comprises a free acid/base form of an agent to be delivered by transdermal electrotransport, and a salt form of the agent, and optionally a permeation enhancer. Methods of enhancing transdermal electrotransport delivery and of forming a composition for the enhancement of transdermal electrotransport drug delivery, and a transdermal electrotransport delivery device (10) utilizing the compositions of the invention are disclosed.

18 Claims, 4 Drawing Sheets

U.S. PATENT DOCUMENTS

| | | | |
|---|---|---|---|
| 5,053,227 | 10/1991 | Chiang et al. | 424/448 |
| 5,059,426 | 10/1991 | Chiang et al. | 424/449 |
| 5,069,908 | 12/1991 | Henley | 424/449 |
| 5,069,909 | 12/1991 | Sharma et al. | 424/449 |
| 5,128,376 | 7/1992 | Saito et al. | 514/772 |
| 5,158,537 | 10/1992 | Haak et al. | 604/20 |
| 5,203,768 | 4/1993 | Haak et al. | 604/20 |
| 5,288,289 | 2/1994 | Haak et al. | 604/20 |
| 5,302,172 | 4/1994 | Sage, Jr. et al. | 604/20 |
| 5,320,597 | 6/1994 | Sage, Jr. et al. | 604/20 |
| 5,320,598 | 6/1994 | Haak et al. | 604/20 |
| 5,328,455 | 7/1994 | Lloyd et al. | 604/20 |
| 5,380,271 | 1/1995 | Gyory | 604/20 |
| 5,395,310 | 3/1995 | Untereker et al. | 604/20 |
| 5,423,739 | 6/1995 | Phipps et al. | 604/20 |
| 5,450,845 | 9/1995 | Axelgaard | 600/382 |
| 5,464,387 | 11/1995 | Haak et al. | 604/20 |
| 5,539,972 | 7/1996 | Gyory et al. | 604/20 |
| 5,540,669 | 7/1996 | Sage, Jr. et al. | 604/290 |
| 5,795,321 | 8/1998 | McArthur et al. | 604/20 |
| 5,840,056 | 11/1998 | Atanasoska | 604/20 |

COMPOSITION AND METHOD OF ENHANCING ELECTROTRANSPORT AGENT DELIVERY

TECHNICAL FIELD

This invention relates to the delivery of agents through a body surface by electrotransport. More particularly, the invention relates to the enhancement of agent delivery with the aid of specific compositions which control the pH while avoiding the addition of competing ions in the composition.

BACKGROUND ART

The transdermal delivery of drugs, by diffusion through the epidermis, offers improvements over more traditional delivery methods, such as subcutaneous injections and oral delivery. Transdermal drug delivery by passive diffusion avoids the hepatic first pass effect encountered with oral drug delivery. Transdermal drug delivery also eliminates patient discomfort associated with subcutaneous injections. In addition, transdermal delivery can provide more uniform concentrations of drug in the bloodstream of the patient over time due to the extended controlled delivery profiles of certain patches. The term "transdermal" delivery, broadly encompasses the delivery of an agent through a body surface, such as the skin, mucosa, or nails of an animal.

The skin functions as the primary barrier to the transdermal penetration of materials into the body and represents the body's major resistance to the transdermal delivery of therapeutic agents such as drugs. To date, efforts have been focussed on reducing the physical resistance or enhancing the permeability of the skin for the delivery of the therapeutic agent by means of passive diffusion. Various methods for increasing the rate of transdermal drug diffusion have been used. For example, drug-impermeable backing layers made of metal, plastic and other materials have been employed in skin patches in order to limit diffusion of drugs away from the skin, increase the hydration of the skin and, thereby, increase the diffusion of drugs through the skin. Increases in the rate of absorption of agents through the skin have been produced by varying the temperature and the relative humidity of the atmosphere adjacent to the skin. Other efforts have been directed at abrading or piercing the skin by mechanically disrupting its outermost stratum corneum layer. Chemical absorption promoters (also referred to as flux enhancers or permeation enhancers) have also been utilized, both as integral components of transdermal therapeutic drug delivery devices compositions or applied to the skin as a pretreatment step before applying the transdermal patch.

The utility of fatty acid permeation enhancers in passive transdermal drug delivery has been previously recognized. (see, for example, U.S. Pat. Nos. 5,045,553 and 5,023,085 (fatty acid with additional cycloketone). Similarly, U.S. Pat. Nos. 5,069,909 (for buprenorphine), 5,001,139 and 4,892,737 disclose the use of fatty acid esters in mixtures with other enhancers for passive transdermal delivery. More generally, $C_5-C_{30}$ aliphatic monocarboxylic acids are disclosed as transdermal drug permeation enhancers in U.S. Pat. No. 4,731,241 for the passive delivery of Nethoxycarbonyl-3-morpholino sydnonimine. U.S. Pat. No. 4,892,737 utilizes a mixture of quaternary ammonium salts with saturated and unsaturated aliphatic carboxylic acids for the passive transdermal electrotransport of agents. U.S. Pat. No. 4,882,163 passively delivers monoxidine with the aid of an alkyl aliphatic acid of at least 12 C-atoms. In U.S. Pat. No. 4,637,930, $C_6-C_{12}$ fatty acid esters are used for the delivery of nicardipine hydrochloride.

A composition for the passive delivery of salicylic acid, which comprises aliphatic diols, an ester of a mono- or polyhydric alcohol and a saturated fatty acid is disclosed in published PCT patent application WO 90/08507. A composition containing salicylic acid, an aliphatic 1,2-diol such as propane- or butane-diol, and a fatty oil, such as triglycerides and their fatty acid derivatives, is disclosed in published PCT patent application WO 89/00853. U.S. Pat. Nos. 4,605,670 and 5,128,376, in addition, disclose the passive percutaneous administration of an active agent in a composition containing a mixture of (1) an ester of a $C_7-C_{18}$ aliphatic acid and an alcohol, a $C_8-C_{26}$ aliphatic monoalcohol, or mixtures thereof, and (2) $C_4-C_6$ cyclic amides such as pyrrolidones, and diols, triols, or mixtures thereof.

These passive methods have generally had only limited success in significantly increasing the transdermal flux of drug.

Transdermal drug permeation rates (fluxes) can also be increased over that obtained with passive diffusion by employing electrically assisted, ie, electrotransport delivery. The term "electrotransport" as used herein refers to delivery of an agent through a body surface with the assistance of an electrical field. Electrotransport, thus, refers generally to the passage of an agent through a body surface, such as the skin, mucous membranes, or nails, which is at least partially induced by applying an electrical current through the surface. Many therapeutic agents, including drugs, may be introduced into the human body by electrotransport. The electrotransport of an agent through a body surface may be attained by one or more of several known phenomena. One widely used electrotransport phenomenon is iontophoresis, which involves the electrically induced transport of charged ions. Electroosmosis, another type of electrotransport, involves the movement of a liquid, which liquid contains one or more therapeutic agent(s) dissolved therein, through a biological membrane under the influence of an electrical field. Electroporation, still another type of electrotransport, involves the movement of an agent through transiently-created pores formed in a biological membrane under the influence of an electric field. When any given agent is electrotransported, more than one of these phenomena, including the phenomenon of passive diffusion, may occur simultaneously to some extent. The term electrotransport, as used herein, is given its broadest possible interpretation to include the electrically induced or enhanced transport of charged species, uncharged species, or mixtures thereof, regardless of the specific mechanism(s) by which the agent (s) is(are) actually transported.

Electrotransport devices require at least two electrodes, both being in electrical contact with some portion of the skin, nails, mucous membrane, or other membrane surfaces of the body. One electrode, commonly referred to as the "donor" or "active" electrode, is the electrode from which the therapeutic agent, such as a drug or prodrug, is delivered into the body. The other electrode, typically termed the "counter" or "return" electrode, serves to close the electrical circuit through the body. For example, if a cationic (ie, a positively charged) agent is to be delivered, the anode will be the active or donor electrode while the cathode is the counter electrode. Alternatively, if the agent to be delivered is an anion, i.e. a negatively charged ion, the cathode will be the donor electrode while the anode is the counter electrode. When anionic and cationic drugs need to be delivered at the same time, both the anode and cathode may be used for this purpose and the anionic drug placed in the cathode while the cationic drug is placed in the anode. In addition, electrotransport delivery devices include an electrical power source, typically in the form of one or more batteries, and optionally electrical control circuitry which regulates the flow of electric current through the electrodes and thereby the rate of drug delivery. Alternatively, the power may be supplied, at least in part, by a galvanic couple formed by contacting two electrodes made of dissimilar materials. A complete electrical circuit is formed by electrically contacting one pole of the power source to the donor electrode, the donor electrode to the body, the body to the counter electrode, and the counter electrode to the opposite pole of the power source.

The donor electrode typically includes a reservoir containing a solution of the agent or drug to be delivered. The donor reservoir may take the form of a pouch, a cavity, a porous sponge, a pad, and a pre-formed gel body, among others. The counter electrode likewise typically includes a reservoir containing a biocompatible electrolyte salt solution. Such reservoirs are electrically connected to the anode or cathode of the electrotransport device to provide either a fixed or a renewable source of one or more therapeutic agents or drugs.

It is known that electrotransport drug flux is roughly proportional to the level of electric current applied by the device. However, there is a limit to the current density (current density is the level of electric current (mA) applied by the device divided by the skin contact area ($cm^2$) of the electrodes) which may be comfortably tolerated by a patient. This limit on the level of current density which may be comfortably tolerated by a patient becomes more problematic as the size of the electrotransport system and, therefore, the skin contact areas of the electrodes, is reduced, ie, for electrotransport systems which are designed to be wearable. Thus, there is a limit to the level of electric current which may be applied by any electrotransport device of a given size and this current limit becomes lower as the size or the skin contact area of the device is reduced. In certain instances, electrotransport devices operating at these current limits have been unable to deliver therapeutically effective amounts of drug. In those cases, the incorporation of a permeation enhancer into the electrotransport device may increase the amount of the agent delivered to adequate levels.

In the context of this application, the term "permeation enhancer" includes absorption promoters and surfactants and broadly describes a chemical species which either reduces the physical resistance of a body surface to the passage of an agent therethrough, alters the ionic selectivity of the body surface, increases the electrical conductivity or the permeability of the body surface, and/or increases the number of pathways therethrough. The use of electrotransport enhancers may help reduce the size of the electrotransport device by requiring a reduced electrical potential (ie, voltage) to generate a particular level of electric current (ie, mA) through the skin and thereby reduce the size and/or number of batteries needed to power the device. A reduction in the size of the device also improves patient comfort, and a reduction in the number of batteries reduces the cost of the device.

A limited number of permeation enhancers for the electrotransport delivery of therapeutic agents have been disclosed in the literature. Ethanol has been utilized as an electrotransport enhancer for polypeptides. See Srinivasan et al, J. Pharm. Sci. 79(7):588–91 (1990). In U.S. Pat. No. 4,722,726 to Sanderson et al., the skin surface is treated with an ionic surfactant (eg, sodium lauryl sulfate) to reduce competition with tissue ions migrating outwardly through the skin. U.S. Pat. No. 5,023,085 to Francoeur et al. discloses the use of unsaturated $C_{14}$–$C_{20}$ acids, alcohols, amines, and esters, along with ketones for the iontophoretic delivery of certain drugs. Published PCT Patent Application WO91/16077 discloses the use of fatty acids, such as oleic acid, lauric acid, capric acid, and caprylic acid, as penetration enhancers for the iontophoretic delivery of drugs. European Patent Application 93/300198.4 discloses delivering therapeutic agents transdermally by iontophoresis with the aid of a broadly described group of "lipid modifiers". The modifiers are generally described as having a $C_5$–$C_{28}$ aliphatic chain and moieties such as hemiacetals amids, acetals, alcohols, carboxylic acids, esters, and others, but containing no more than 50 to 60 carbon atoms. Only a few dioxolanes, an aliphatic carbonate, and a pyrrolidone are exemplified.

Many drugs exist in both free acid/base form and a salt form. For example, a base drug may exist in either free base form or in salt form, eg, an acid addition salt. One example of a base drug is lidocaine. In free base form, lidocaine is an amine. Lidocaine is also available as a hydrochloride acid addition salt. Conversely, an acid drug may exist in either free acid form or in the form of a salt, eg, a base addition salt. One example of an acid drug is salicylic acid. This drug also exists as a salt, ie, sodium salicylate. In general, the salt form of a drug is preferred over the free acid or free base form for electrotransport delivery since the salt form generally has much better water solubility and water is the preferred liquid solvent for electrotransport delivery due to its excellent biocompatability. An "acid form" of a drug or other therapeutic agent, as used herein, refers to a form of the agent which is a Lewis acid, i.e. any form of the agent which can attach itself to a molecule with an unshared pair of electrons. Similarly, a "base form" of a drug or other therapeutic agent, as used herein, refers to a form of the agent which possesses an unshared pair of electrons.

In general, many drugs exist in both (1) a salt form, and (2) either a free base or acid form. For example, a drug having an amino group may have an $R_3N$ base form, e.g. lidocaine, or a $R_3N.HCl$ acid addition salt form, e.g. lidocaine hydrochloride, in which a hydrogen atom is associated with, or weakly bonded to, the nitrogen atom of the amino moiety. The base form generally has poor water solubility. This is undesirable in electrotransport systems since water is the preferred liquid solvent for forming a solution of the drug to be delivered by electrotransport. Although the salt forms of drugs are likely to have higher water solubility, the pH produced by the salt form of the drug may not be optimal from the strandpoint of transdermal drug flux. For example, human skin exhibits a degree of permselectivity to charged ions which is dependant upon the pH of the donor solution of an electrotransport device. For anodic donor reservoir solutions, transdermal electrotransport flux of a cationic species (ie, a cationic drug) is optimized when the pH of the donor solution is about 6 to 9, and more preferably about 7.5 to 8. For cathodic donor reservoir solutions, transdermal electrotransport flux of an anionic species (ie, an aninoic drug) is optimized when the pH of the donor solution is about 3 to 6, and more preferably about 3.5 to 5.

A problem which arises with the addition of pH-altering species (eg, an acid or a base) to the drug solution in an electrotransport device is that extraneous ions having the same charge (ie, same sign charge) as the drug are introduced into the solution. These ions generally compete with the therapeutic agent ions for electrotransport through the body surface. For example, the addition of sodium hydroxide to lower the pH of a cationic drug-containing solution will introduce sodium ions into the solution which will compete with the cationic drug for delivery by electrotransport into the patient, and thereby makes the electrotransport delivery less efficient since it takes more electric current to delivery a set amount of drug. A similar competing ion effect can be seen with the addition of permeation enhancers in the form of salts. For example, the addition of sodium laurate as a permeation enhancer to a cationic drug-containing reservoir composition will have two opposing effects. The laurate groups will increase skin permeability, and hence increase the drug delivery rate. On the other hand, the sodium ions will compete with the cationic drug for electrotransport through the body surface and, thus, reduce the efficiency of drug delivery. The sodium ions, in this context, are termed "competing ions". As used herein, the term "competing ions" refers to ionic species having the same charge as the agent to be delivered by electrotransport, and which may take the place of the agent and be delivered through the body surface in its place. Similarly, agents which are used to buffer the pH of a donor reservoir solution can likewise result in the addition of competing ions into the donor reservoir which results in lower efficiency electrotransport drug delivery, ie, less drug is delivered per unit of electrical current applied by the device due to competing ions carrying the current as opposed to the drug ions.

DISCLOSURE OF THE INVENTION

The present invention provides a composition and method of adjusting or setting the pH of a donor solution of an electrotransport device to a level at which the permselectivity of the skin is maximized without undesirably introducing substantial amounts of competing ions to the donor solution. In the case of an anodic donor solution, the solution pH is preferably in the range of about 6 to 9, and more preferably in the range of about 7.5 to 8 in order to maximize transdermal electrotransport flux. In order to raise the pH of an anodic donor solution of an acid addition salt of a base drug to the desired range, the base drug itself is added to the salt solution instead of adding a conventional base (eg, NaOH or KOH) which would introduce competing cations (eg, $Na^+$ or $K^+$) into the donor reservoir. The base drug acts as a proton acceptor which thereby raises the pH of the donor solution without introducing competing ions. Of course, the protonated base drug will have a net positive charge but it is not considered "competing" since it is chemically identical to the drug being delivered by electrotransport. The relative amounts of base drug and drug salt added to the solution will vary depending upon the particular drug salt in solution, the desired concentration of the drug in the solution, the pK of the drug salt and the final desired pH of the donor solution. Those skilled in the art can determine the appropriate relative amounts of base drug and drug salt by routine experimentation following the specific descriptions hereinafter.

In the case of a cathodic donor solution, the solution pH is preferably in the range of about 3 to 6, and more preferably in the range of about 3.5 to 5 in order to maximize transdermal electrotransport flux. In order to lower the pH of a donor solution of a salt of an acid drug to this desired range, the acid drug itself is added to the salt solution instead of a conventional acid (eg, HCl or $H_2SO_4$) which would introduce competing anions (eg, $Cl^-$ or $SO_4^{-2}$) into the donor reservoir. The acid drug acts as a proton donor which thereby lowers the pH of the donor solution without introducing competing ions. Of course, once the proton is donated, the remaining "counter" ion will have a net negative charge but it is not considered "competing" since it is chemically identical to the drug being delivered by electrotransport. The relative amounts of acid drug and drug salt added to the solution will vary depending upon the particular drug salt in solution, the desired concentration of the drug in the solution, the pK of the drug salt and the final desired pH of the donor solution. Those skilled in the art can determine the appropriate relative amounts of acid drug and drug salt by routine experimentation following the specific descriptions hereinafter.

The invention also contemplates an electrotransport delivery device comprising donor and counter electrodes wherein the donor reservoir contains the composition of the invention.

BRIEF DESCRIPTION OF THE DRAWINGS

The invention will now be described in further detail with reference to the accompanying drawings, wherein.

MODES FOR CARRYING OUT THE INVENTION

Figure 1:
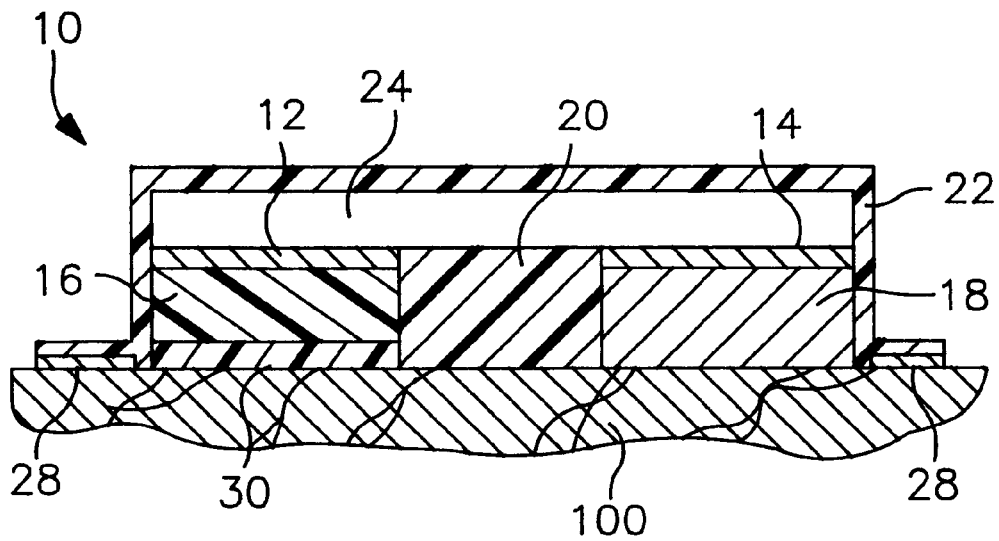
FIG. 1 is a sectional view of an electrotransport agent delivery device which represents one embodiment of the present invention.

The present invention avoids the need to adjust the pH of the donor reservoir composition with an acid or a base which introduces ionic species that compete with therapeutic agent ions for electrotransport delivery through a body surface such as skin. Thus, in accordance with the present invention, acids, bases and/or buffers used to adjust and maintain the pH of a donor reservoir solution in an electrotransport delivery device, which acids, bases and/or buffers are structurally unrelated to the agent being delivered, are avoided or minimized.

The pH of the drug-containing formulation in the donor reservoir of an electrotransport device is controlled and the delivery of the agent enhanced, in accordance with the present invention, while avoiding the use of chemically unrelated acids, bases, and buffers. The pH may also be varied, at least in part, by varying the ratio of the various forms of the delivery agent in the donor reservoir, i.e. by varying the concentrations of the agent in its acid/base and salt forms.

Optionally, the anodic or cathodic donor solution also contains a body surface (eg, skin) permeation enhancer. Any known electrotransport permeation enhancer may be used in conjunction with the acid/base and salt formulations of the present invention. Examples of suitable permeation enhancers include alcohols such as ethanol; mixtures of lower and higher alcohol mixtures such as those disclosed in U.S. patent application Ser. No. 339,092 filed Nov. 14, 1994; glycols, surfactants such as those disclosed in Sanderson et al U.S. Pat. No. 4,722,726; fatty acids such as those disclosed in Francoeur et al U.S. Pat. No. 5,023,085; solid/semi-solid permeation enhancers such as those disclosed in U.S. patent application Ser. No. 338,924 filed Nov. 14, 1994;

non-ionic and zwitterionic surfactants such as those disclosed in U.S. patent application Ser. No. 341,246 filed Nov. 17, 1994. The disclosures of the above listed patents and patent applications are incorporated herein by reference.

The concentration of the permeation enhancer in the delivery composition may vary substantially with each delivery agent, and/or enhancer utilized, and with the specific delivery conditions employed. Broadly speaking, the permeation enhancer may be present in amounts up to about 25 wt % of the donor solution.

The concentration of the agent in the composition depends on various factors, including its potency, the magnitude and the duration of the applied current, the concentration of the enhancer, and the pH of the composition. Generally, the concentration of the agent in the composition ranges from about 10 to 100,000 μg/ml, and more preferably, from about 100 to about 50,000 μg/ml. Similarly, the preferred ratio of the different forms of the agent in the composition is also a function of the specific delivery conditions. Generally, from 1 to 99 wt % of the total agent concentration is added in salt form, and more preferably, about 10 to 90 wt %.

The most preferred pH of the donor formulation will depend upon a number of factors in addition to the charge of the therapeutic agent ions (i.e., whether the agent is cationic or anionic) including the particular therapeutic agent being delivered, the pK of the agent and its solubility in the (eg, aqueous) liquid solvent, the need to maximize the electrotransport delivery rate, and the degree of irritation and sensitization encountered during electrotransport delivery of the agent. In general however, cationic therapeutic agents are preferably delivered from a donor reservoir having a pH of about 6 to 9, and more preferably about 7.5 to 8, whereas anionic agents are preferably delivered at a pH of about 3 to 6, and more preferably about 3.5 to 5.

This invention is useful for the delivery of a broad class of agents that are deliverable through body surfaces and membranes, including the skin, mucosa and nails. Examples of cationic therapeutic agents which may be delivered by electrotransport in accordance with the present invention include lidocaine, fentanyl, metoclopramide, ondansetron, verapamil and terbutaline, among others. Examples of anionic therapeutic agents which may be delivered in accordance with the present invention include ketoprofen, indomethacin, diclofenac, cromolyn, and salicylate, among others. The above listed therapeutic agents are merely exemplary of the many drugs and other therapeutic agents which may be delivered in accordance with the present invention. As used herein, the expression "agent" is intended in its broadest sense as any pharmaceutically-acceptable agent, and preferably therapeutically active substances, such as drugs or prodrugs, which are delivered to a living organism to produce a desired, and usually beneficial, effect. In general, this includes therapeutic agents in all of the major therapeutic areas including, but not limited to, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetic agents; antidiarrheals; antihistamines; antiinflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetrics; xanthine derivatives; cardiovascular preparations including calcium channel blockers such as nifedipine; betaagonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous systems stimulants; cough and cold preparations; decongestants; diagnostics; hormones such as parathyroid hormones; hypnotics; immunosuppressives; muscle relaxants; parasympatholytics; arasympathomimetrics; prostaglandins; proteins; peptides; psychostimulants; sedatives and tranquilizers.

More specifically, this invention is useful in the electrotransport delivery of agents which may be produced in both acid/base form and salt form. An "acid form" of a therapeutic agent, as used herein, refers to a form of the agent which is a Lewis acid, i.e. any form of the agent which can attach itself to a chemical moiety with an unshared pair of electrons. A "base form" of a therapeutic agent, as used herein, refers to a form of the agent which possesses an unshared pair of electrons. A "salt form" of a therapeutic agent, as used herein, is any form of the agent which carries a net positive or negative charge when dissolved in a polar solvent, eg, water.

The invention, therefore, may be applied to a wide variety of agents which have both (i) a free acid or free base form, and (ii) a salt form. A preferred application of the invention has particular utility in the electrotransport delivery of drugs having amine groups. Typically, agents having amino groups have an $R_3N$, base form e.g. lidocaine, or an $R_3N$—$H^+$ acid addition salt form, e.g. lidocaine hydrochloride, in which a hydrogen atom is associated with, or weakly bonded to, the nitrogen atom. Thus, this preferred group of agents has a base form and a protonated form. Examples of preferred amine-containing agents having a protonated form in accordance with this embodiment of the present invention include, without limitation, buspirone, diltiazem, encainide, fentanyl, lidocaine, metoclopramide, midazolam, nicardipine, prazosin, scopolamine, tetracaine, and verapamil, among others. For example, a useful composition for the electrotransport delivery of lidocaine in accordance with this invention is that comprising a lidocaine base, a lidocaine salt, such as its hydrochloride salt, and optionally an alkyl acid enhancer, such as lauric acid. More preferably, the composition further comprises a solvent, such as ethanol, and water.

Another preferred application of the invention is in the controlled delivery of peptides, polypeptides, proteins, and other macromolecules which are otherwise difficult to deliver transdermally or transmucosally because of their size. These macromolecular substances typically have a molecular weight of at least about 300 Daltons, and more typically, a molecular weight in the range of about 300 to 40,000 Daltons. However, smaller and larger peptides are also deliverable in accordance to this invention. Examples of peptides and proteins which may be delivered in accordance with the present invention include, without limitation, LHRH, LHRH analogs such as buserelin, gonadorelin, naphrelin and leuprolide, GHRH, GHRF, insulin, insulinotropin, calcitonin, octreotide, endorphin, TRH, NT-36 [chemical name: N-[[(s)-4-oxo-2-azetidinyl] carbonyl]-L-histidyl-L-prolinamide], liprecin, pituitary hormones, e.g. HGH, HMG, desmopressin acetate, follicle luteoids, α-ANF, growth factor releasing factor (GFRF), β-MSH, somatostatin, bradykinin, somatotropin, platelet-derived growth factor, asparaginase, chymopapain, cholecystokinin, chorionic gonadotropin, corticotropin (ACTH), erythropoietin, epoprostenol (platelet aggregation inhibitor), glucagon, HCG, hirulog, hirudin analogs, hyaluronidase, interferon, interleukins, menotropins, e.g. urofollitropin (FSH) and LH, oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta, in their base and acid forms or as an agent-enhancer compound.

Referring now to FIG. 1, one example of a unitary electrotransport device 10 useful in accordance with the present invention is illustrated. The device 10 has two current distributing members or electrodes, made of electrically conductive materials, referred to herein as donor electrode 12 and counter electrode 14. The electrodes may be composed of any materials which are sufficiently electrically conductive including, without limitation thereto, silver, silver chloride, zinc, and stainless steel. The electrodes may have various forms including metal foil, screen, coatings and polymer matrices loaded with electrically conductive fillers such as powdered metal, e.g. silver or carbon. Such matrices may be formed by conventional processes such as extrusion, calendering, film evaporation, or spray coating. In FIG. 1, the donor and counter electrodes 12 and 14 are positioned adjacent to, and in electrical contact with, the donor reservoir 16 and the counter reservoir 18, respectively. The donor reservoir 16 contains the agent to be delivered, while the counter reservoir 18 contains a biocompatible electrolytic salt. The reservoirs are formed of any material adapted to absorb and hold a sufficient quantity of liquid therein in order to permit the passage of agent therethrough by electrotransport. Preferably, the reservoirs contain one or more hydrophilic polymers such as polyvinylpyrrolidone, polyvinyl alcohol, or polyethylene glycols, and optionally one or more hydrophobic polymers such as polyisobutylene, polyethylene, or polypropylene. The donor electrode 12 and donor reservoir 16 are separated from the counter electrode 14 and the optional counter reservoir 18 by an electrical insulator 20. The insulator 20, may be an air gap or it may be composed of a material which neither conducts electrons nor ions to a substantial extent, and prevents device 10 from short-circuiting through an electrical path which does not include the body surface 100 to which the device 10 is applied. The device 10 optionally includes a backing layer 22 composed of a water-proof and preferably electrically insulating material. Device 10 has an electronic circuit, illustrated schematically in FIG. 1 as a layer 24, which includes an electric power source, e.g. one or more batteries, therein. Typically, the electronic circuit layer 24 is relatively thin and preferably comprised of electronically conductive pathways printed, painted or otherwise deposited on a thin, flexible substrate such as, for example, a film or polymeric web, e.g. the electronic circuit layer 24 is a printed flexible circuit. In addition to the power source, the electronic circuit layer 24 may also include one or more electronic components which control the level, waveform shape, polarity, timing, etc., of the electric current applied by device 10. For example, circuit layer 24 may contain one or more of a electronic control circuitry such as a current controller, e.g. a resistor or a transistor-based current control circuit, an on/off switch, and/or a microprocessor adapted to control the current output of the power source over time. The outputs of circuit layer 24 are electrically connected to electrodes 12 and 14 such that each electrode is in electrical contact with an opposite pole of the power source within circuit layer 24. The device 10 adheres to the body surface 100 in this embodiment by means of a peripheral adhesive layer 28. Optionally, the device may contain an in-line adhesive layer, i.e. an adhesive layer covering an entire surface of the electrotransport device. This surface is then applied to the body surface. An in-line adhesive must be ion-transmitting, i.e. donor agent ions must be capable of penetrating the adhesive layer to reach the body surface 100. An optional flux control membrane 30 is positioned between donor reservoir 16 and body surface 100 in order to limit or control the amount of passive, i.e. not electrically assisted, flux of agent to body surface 100.

Having thus generally described the invention and certain preferred embodiments thereof, the invention will be further described by reference to the following detailed examples.

EXAMPLES

Example 1

Figure 2:
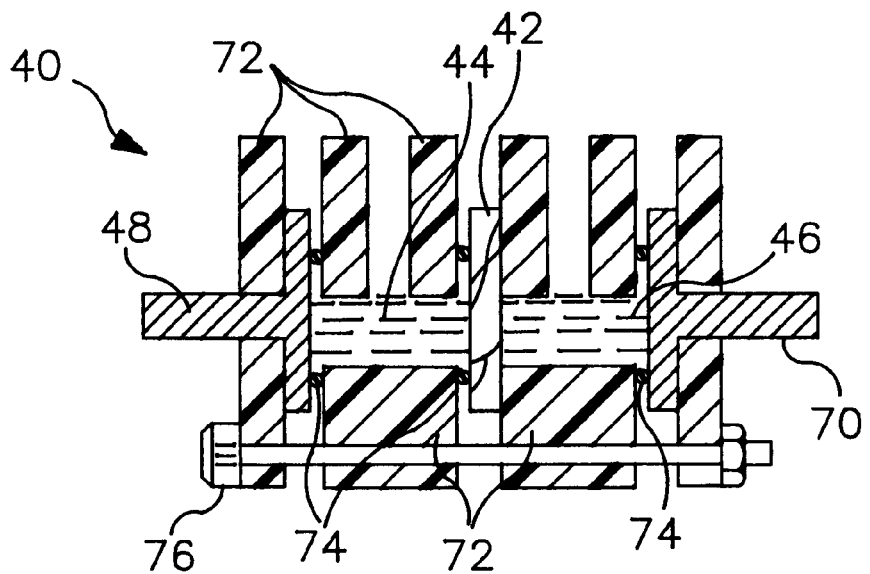
FIG. 2 is a schematic view of an electrotransport system, with parts shown in section, having donor and counter electrodes connected to a remote electrical power source.

Effect of Base:Salt Agent Ratio on pH and Transdermal Electrotransport Lidocaine Flux In the following experiments, pH adjusted aqueous solutions of lidocaine were used as donor solutions to measure in vitro transdermal electrotransport flux of lidocaine. Pieces of heat stripped human epidermis obtained from the thigh and breast of human cadavers were mounted in a 2-compartment electrotransport permeation cell illustrated in FIG. 2. Cell 40 was composed predominately of polycarbonate pieces 72 held together with a bolt and nut 76. Cell 40 had a silver foil anodic donor electrode 48 and a Ag/AgCl loaded ethylene vinyl acetate polymer film as the cathodic receptor electrode 70. The donor and receptor electrodes 48,70 were electrically connected to a galvanostat (not shown in FIG. 2) which was set to apply a constant electric current of 126 $\mu$A. The area of each skin sample 42 exposed to electrotransport was about 1.26 cm$^2$ and the volume of each of the donor compartment 44 and the receptor compartment 46 was about 2 mL. The compartments 44 and 46 were sealed using O-rings 74. Solutions containing selected combinations of lidocaine HCl and lidocaine base were placed in the donor compartment 44. Dulbecco's phosphate buffered saline (an aqueous 0.15 N NaCl solution with minor amounts of other ions, buffered to pH 7.0) was added to the receptor compartment 46. The permeation cell 40 was maintained at about 32° C. throughout each flux experiment. The rate of transdermal electrotransport of the drug was determined by periodically sampling the receptor solution and assaying for lidocaine content. The resistance of the skin under the influence of the applied electrical current was calculated from the voltage applied by the galvanostat using Ohm's Law ($R_{skin} = \Delta V/i$).

An aqueous donor solution of lidocaine (both hydrochloride salt form and free base form) was placed in the donor compartment and its molar amount was held essentially constant, at about 198 mmoles, for all experiments. The pH of the donor solutions was modified by varying the ratio of lidocaine base to lidocaine HCl. The flux of lidocaine was measured for a 4 hr. period, during which a constant electric current of 126 $\mu$A was applied. Two identical experiments were conducted at pHs 4.95 and 7.35, one at pH 6.85, and three at pH 6.25. The lidocaine flux values obtained were averaged, and are shown in Table 1 below.

TABLE 1

| pH | 4.95 | 6.25 | 6.85 | 7.35 |
|---|---|---|---|---|
| Current Applied ($\mu$A) | 126 | 126 | 126 | 126 |
| Lidocaine Base (mmoles) | 0 | 2.1 | 6.0 | 20.3 |
| Lidocaine HCl (mmoles) | 199 | 195 | 191 | 179 |
| Average Flux* (0 to 1 hr) | 51 | 54 | 66 | 101 |
| Average Flux* (1 to 2 hrs) | 84 | 100 | 101 | 164 |
| Average Flux* (2 to 3 hrs) | 108 | 107 | 118 | 175 |
| Average Flux* (3 to 4 hrs) | 127 | 118 | 142 | 181 |
| Average Flux* (0 to 4 hrs) | 100 | 95 | 107 | 155 |

*$\mu g/cm^2 hr$

As can be seen from the data presented in Table 1 above, among the four formulations tested, the transdermal electrotransport lidocaine flux was greatest when the formulation contained the greatest amount (ie, 20.3 mmoles) of lidocaine base, ie, at pH 7.35.

Example 2

Lidocaine Donor Gel Formulations

Thirteen separate lidocaine donor reservoir gel formulations were prepared with the contents shown in Table 2 below.

TABLE 2

| | Agent Formulation No. | | | | | | | | | | | | |
|---|---|---|---|---|---|---|---|---|---|---|---|---|---|
| | 1 (wt %) | 2 (wt %) | 3 (wt %) | 4 (wt %) | 5 (wt %) | 6 (wt %) | 7 (wt %) | 8 (wt %) | 9 (wt %) | 10 (wt %) | 11 (wt %) | 12 (wt %) | 13 (wt %) |
| PVOH | 8.3 | 12.6 | 13.2 | 10.1 | 11.9 | 13.0 | 13.0 | 13.0 | 12.6 | 13.0 | 11.6 | 11.8 | 11.6 |
| Cholestyramine | — | — | — | — | — | — | — | — | — | 5.0 | — | — | — |
| Lidocaine HCl | 4.2 | 6.3 | 6.6 | 4.8 | 5.9 | 4.5 | 4.7 | 4.5 | 4.4 | 4.5 | 2.0 | 2.0 | 2.0 |
| Lidocaine Base | 8.7 | 1.3 | 0.6 | 1.0 | 1.2 | 0.5 | 0.3 | 0.5 | 0.5 | 0.5 | 0.4 | 0.4 | 0.4 |
| ETOH | 34.6 | 12.7 | 5.9 | 9.1 | 17.6 | 5.0 | 5.0 | 5.0 | 4.8 | 5.0 | 25.0 | 25.4 | 24.8 |
| Lauric Acid | — | — | — | — | — | — | — | 0.2 | — | — | 0.2 | 0.2 | 0.2 |
| Glycerol | — | — | 3.4 | 9.1 | — | — | — | — | 3.9 | — | — | — | — |
| Water | 44.3 | 67.1 | 70.3 | 65.9 | 63.5 | 77.0 | 77.0 | 76.8 | 73.9 | 72.0 | 60.8 | 60.2 | 59.8 |
| pH | 6.90 | 7.03 | 6.69 | 6.94 | 6.84 | 6.93 | 6.77 | 6.83 | 7.04 | 7.04 | 6.7 | — | — |

Polyvinyl alcohol based hydrogels having a thickness of 1.6 mm (1/16 inch) and a diameter of 1.3 cm (1/2 inch) were prepared by mixing the components, into a preformed aqueous polyvinyl alcohol (PVOH) stock solution, at 50° C. in a beaker with a paddle type mixer to obtain each of formulations #1 through #11. Formulation #10 also contained 5 wt % cholestyramine resin (sold by Rohm & Haas, Philadelphia, Pa.), a strongly basic ion-exchange hydrophilic resin in the chloride form, consisting of styrene divinylbenzene copolymer with quaternary ammonium functional groups. Each of the formulations was then pipetted into foam molds having cylindrically shaped cavities and cured overnight at −20° C. The gels were removed from the molds and allowed to attain room temperature. The formulations #12 and #13 were prepared in a similar manner as formulations #1 through #11 except the gels were cured at −80° C.

A Dulbecco's phosphate buffered saline (PBS) solution was prepared by mixing 59.61 g of 10×DPBS with 45.0 g water pH 7.39, adding 1.00 ml of 1M HCl, pH 6.91, then water to 500.01 g, pH 6.92–6.93. The solution was stored at 4° C. and used in the reservoir of the receptor electrode.

The in vitro transdermal electrotransport flux of lidocaine was measured using gel formulations #6 and #8 described in Table 2 and above, with two gels being tested for each formulation.

Figure 3:
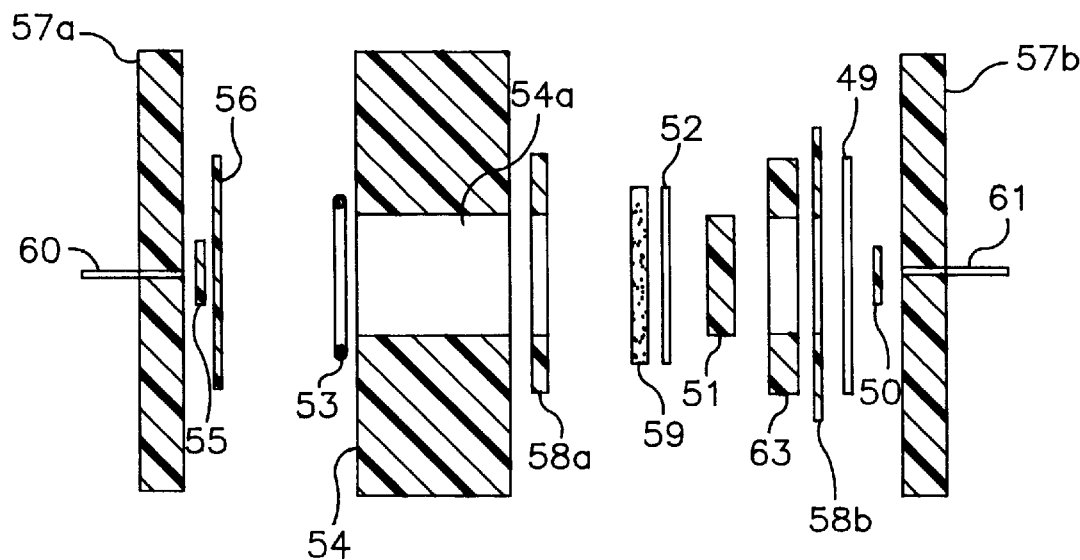
FIG. 3 is a sectional exploded view of a device used to perform in vitro electrotransport flux experiments in the Examples.

The device used to perform the in vitro flux experiments is shown in FIG. 3. The device was set up by placing a piece of electrically conductive polyisobutylene adhesive 55 onto the end of lead 60. The leads 59, 60 were electrically connected to a galvanostat, which applies the necessary voltage to deliver a predetermined level of DC electric current, to the leads 60, 61 and the electrodes 49, 56 such that each electrode is electrical contact with an opposite pole of the galvanostat. Onto the adhesive 55 was placed a silver chloride-loaded ethylene vinyl acetate film 56, and on the film 56 was placed an O-ring 53, which was also in contact with a receptor reservoir housing 54 having a cavity 54a containing a solution of Dulbecco's phosphate buffered saline. On the other side of the housing 54 was placed a 2-sided tape 58a to affix the skin sample 52 thereto. The skin sample was laid against an open weave polypropylene fabric 59 for added support. On the other side of the skin sample 52 was placed a gel 51 with the formulation to be tested. The gel 51 was maintained in place by a foam support 63, and opposite the side of the gel was placed a silver foil donor electrode 49 held in place with 2-sided tape 58b. A second piece of electrically conductive adhesive 50 was placed on the other side of the silver electrode 49, and then a second end piece 57b was put in place so that adhesive 50 was in contact with a second lead 61 which was connected to the galvanostat. The entire device was clamped securely together using bolts (not shown) passing through end pieces 57a, 57b and housing 54. Different gels 51 containing the two lidocaine formulations (#6 and #8) were used.

Figure 4:
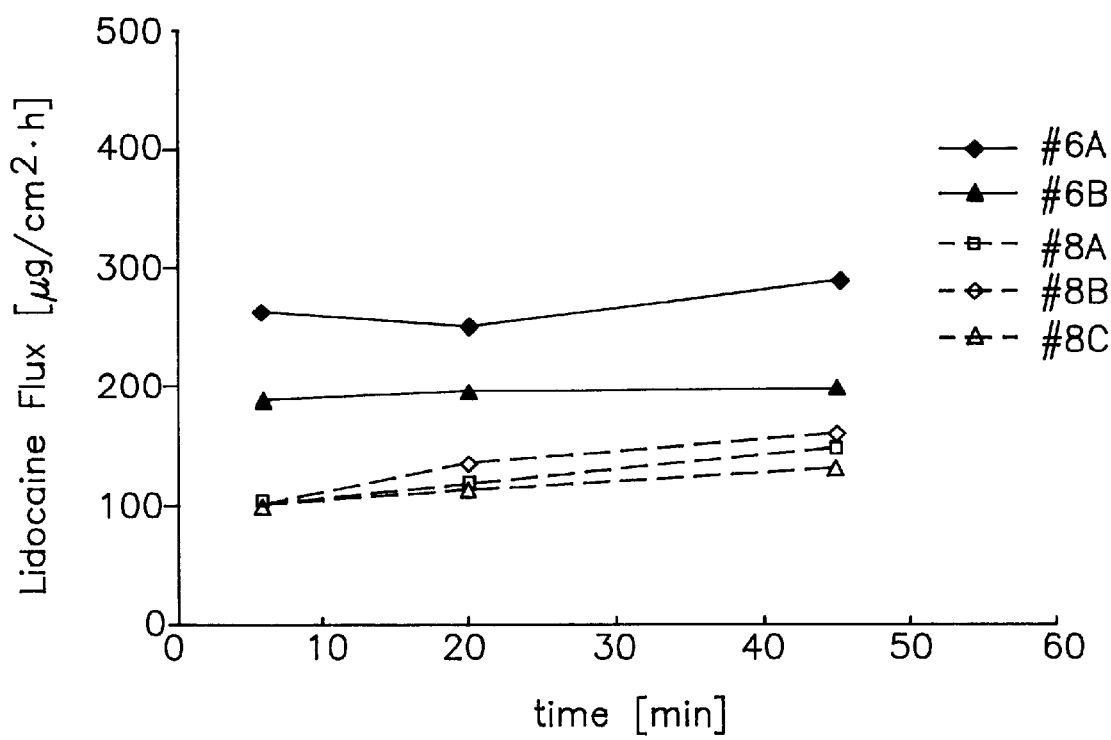
FIG. 4 is a graph of lidocaine flux versus time for the gel formulations tested in Example 2.

The galvanostat was set to apply an electric current of 127 $\mu$A, and samples from the receptor reservoir were taken at 2, 10, 30 and 60 minutes after starting the applied current. At 60 minutes, the current was turned off and the receptor was not refilled. Each of the gel formulations #6 and #8 was tested in triplicate and the results are plotted in FIG. 4.

Figure 5:
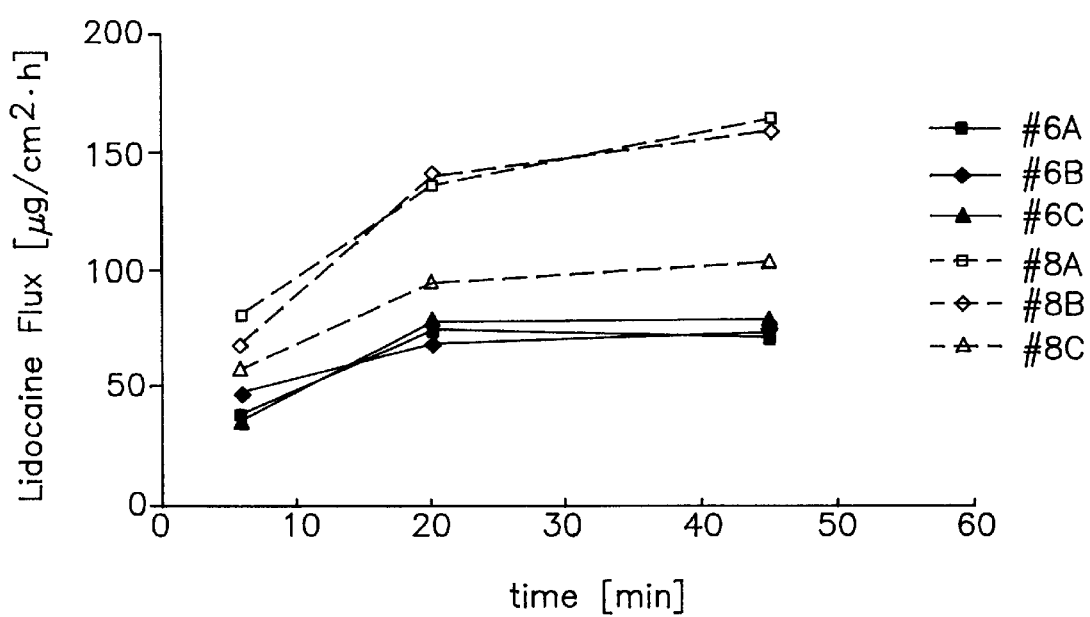
FIG. 5 is a graph of lidocaine flux versus time for donor gel formulations tested in Examples 2.

A second flux experiment was performed with the same device and under the same conditions described above. The results are plotted in FIG. 5.

Example 3

Lidocaine/Epinephrine Comparative Flux Experiment

Polyvinyl alcohol based hydrogels were made using the methods described in Example 2. Two different formulations were made having the compositions described in Table 3 below. Composition #14 contained only lidocaine hydrochloride (ie, no lidocaine base) and had a pH of 3.68 whereas formulation #15 contained a mix of lidocaine HCl and lidocaine base and had a higher pH (ie, pH 6.42).

TABLE 3

| Formulation No. | 14 (wt %) | 15 (wt %) |
|---|---|---|
| PVOH | 13.01 | 13.23 |
| Lidocaine HCl | 2.50 | 2.32 |
| Lidocaine base | | 0.17 |
| Epinephrine bitartrate | 0.09 | 0.09 |
| Water | 84.39 | 84.18 |
| pH | 3.68 | 6.42 |

The formulation 14 and 15 gels were subjected to transdermal flux experiments using heat stripped chest and breast skin from human cadavers using the electrotransport permeation cell described in Example 2 and FIG. 3. Measurements were taken from the receptor compartment of the cell at 10 minutes, 30 minutes, 60 minutes, and 90 minutes after start of application of electrotransport current. The transdermal flux of both lidocaine and epinephrine did not have a significant statistical difference between formulation 14 and 15. The explanation for this is believed to be that lidocaine transdermal flux does not show significant enhancement until the pH of the donor formulation rises above about pH 7. See, for example, the fourth column. While lidocaine appears to exhibit enhanced transdermal electrotransport flux at pH's above about 7, other cationic drugs are likely to have slightly different "minimum pH flux enhancement" levels within the general range of about pH 6 to 9.

Having thus generally described the invention and certain preferred embodiments thereof, it will be readily apparent to a person with skill in the art that various modifications to the invention may be made without departing from the scope of this invention.

We claim:

1. An anodic donor reservoir composition comprising:
    a solution of the acid addition salt of a base therapeutic agent wherein the pH of said solution has been adjusted to within a predetermined range by the addition of base therapeutic agent and wherein the water content is at least about 44.3 wt %.

2. The anodic donor reservoir composition of claim 1 wherein the predetermined range is a range of about pH 6.0 to about pH 9.0.

3. The anodic donor reservoir composition of claim 2 wherein the solvent is water.

4. The anodic donor reservoir composition of claim 3 further comprising a co-solvent.

5. The anodic donor reservoir composition of claim 4 wherein said co-solvent is ethanol.

6. The anodic donor reservoir composition of claim 1 wherein said base therapeutic agent is a local anesthetic.

7. The anodic donor reservoir composition of claim 6 wherein said local anesthetic is selected from the group consisting of lidocaine, procaine, and tetracaine.

8. The anodic donor reservoir composition of claim 1 wherein said base therapeutic agent is an analgesic.

9. The anodic donor reservoir composition of claim 8 wherein said analgesic is selected from the group consisting of fentanyl, sufentanil and buprenorphine.

10. A process of making an anodic donor reservoir composition comprising the steps of:
    dissolving a desired amount of the acid addition salt of a base therapeutic agent in a suitable solvent, and
    adding said base therapeutic agent until said composition has a pH within a predetermined range and wherein the final concentration of water in the composition is at least about 44.3 wt %.

11. The process of making an anodic donor reservoir composition of claim 10 wherein said predetermined pH range is a range from about pH 6.0 to about pH 9.0.

12. The process of making an anodic donor composition of claim 11 wherein said suitable solvent is water.

13. The process of making an anodic donor composition of claim 12 wherein said suitable solvent includes a co-solvent.

14. The process of making an anodic donor composition of claim 13 wherein said co-solvent is ethanol.

15. The process of making an anodic donor composition of claim 10 wherein said base therapeutic agent is a local anesthetic.

16. The process of making an anodic donor composition of claim 15 wherein said local anesthetic is selected from the group consisting of lidocaine, procaine, and tetracaine.

17. The process of making an anodic donor composition of claim 10 wherein said base therapeutic agent is an analgesic.

18. The process of making an anodic donor composition of claim 17 wherein said analgesic is selected from the group consisting of fentanyl, sufentanil and buprenorphine.

* * * * *